United States Patent
Enomoto et al.

(10) Patent No.: US 7,884,281 B2
(45) Date of Patent: Feb. 8, 2011

(54) PHOTOELECTRIC TRANSFER MATERIAL, MANUFACTURING METHOD THEREOF, PHOTOELECTRIC TRANSFER ELEMENT AND MANUFACTURING METHOD THEREOF

(75) Inventors: Masashi Enomoto, Tokyo (JP); Myung-Seok Choi, Kanagawa (JP); Yoshiaki Kobuke, Kyoto (JP); Akiharu Satake, Nara (JP)

(73) Assignee: Sony Corporation, Tokyo (JP)

( * ) Notice: Subject to any disclaimer, the term of this patent is extended or adjusted under 35 U.S.C. 154(b) by 59 days.

(21) Appl. No.: 11/033,587

(22) Filed: Jan. 11, 2005

(65) Prior Publication Data

US 2005/0211293 A1 Sep. 29, 2005

(30) Foreign Application Priority Data

Jan. 19, 2004 (JP) ............................ P2004-010068

(51) Int. Cl.
*H01L 31/00* (2006.01)
(52) U.S. Cl. ........................ 136/263; 136/252; 438/82
(58) Field of Classification Search ................. 136/263, 136/252; 257/40, 431; 252/501.1, 510, 519.2, 252/519.21; 438/57, 82
See application file for complete search history.

(56) References Cited

U.S. PATENT DOCUMENTS

| | | | | |
|---|---|---|---|---|
| 5,006,915 | A * | 4/1991 | Yoshikawa et al. | 257/40 |
| 5,331,183 | A | 7/1994 | Sariciftci et al. | |
| 6,596,935 | B2 * | 7/2003 | Lindsey et al. | 136/263 |
| 6,602,998 | B2 * | 8/2003 | Kobuke et al. | 540/145 |
| 2001/0018515 | A1 * | 8/2001 | Kobuke et al. | 540/145 |
| 2003/0178630 | A1 * | 9/2003 | Maruyama | 257/98 |
| 2004/0072988 | A1 * | 4/2004 | Kobuke et al. | 528/395 |
| 2004/0202876 | A1 * | 10/2004 | Kobuke et al. | 428/457 |
| 2005/0061364 | A1 * | 3/2005 | Peumans et al. | 136/263 |

FOREIGN PATENT DOCUMENTS

| | | |
|---|---|---|
| JP | 2000-261016 | 9/2000 |
| JP | 2000-306605 | 11/2000 |
| JP | 2001-007366 | 1/2001 |
| JP | 2001-199715 | 7/2001 |

(Continued)

OTHER PUBLICATIONS

Yu, G. et al., "Polymer Photovoltaic Cells: Enhanced Efficiencies via a Network of Internal Donor-Acceptor Heterojunctions". Science. 270, 1789-1791. (1995).*

(Continued)

*Primary Examiner*—Jeffrey T Barton
(74) *Attorney, Agent, or Firm*—K&L Gates LLP

(57) ABSTRACT

A photoelectric transfer material, manufacturing method thereof, photoelectric transfer element and manufacturing method thereof are provided. In an organic photoelectric transfer element of an organic solar cell or other like device, the photoelectric transfer material is composed of a conductive polymer such as MEH-PPV, electronic acceptor such as a fullerene derivative and antenna porphyrin aggregate. The photoelectric transfer material can be made by coating a mixed solution of the conductive polymer, electron acceptor and antenna porphyrin aggregate by spin coating, for example. This photoelectric transfer material and a photoelectric transfer element using the material exhibit high photoelectric transfer efficiency because of small electric resistance and high sunlight usage efficiency, and simultaneously exhibit stability.

7 Claims, 8 Drawing Sheets

FOREIGN PATENT DOCUMENTS

| | | | | |
|---|---|---|---|---|
| JP | 2001-253883 | | | 9/2001 |
| JP | 2001-303022 | | | 10/2001 |
| JP | 2002-025635 | | | 1/2002 |
| JP | 2002-335004 | | | 11/2002 |
| JP | 2002-335004 | A | * | 11/2002 |
| JP | 2003-300982 | | | 10/2003 |
| JP | 2003-300983 | | | 10/2003 |
| JP | 2004-266100 | | | 9/2004 |
| JP | 2004-335737 | | | 11/2004 |
| JP | 2005-203659 | A | * | 7/2005 |
| WO | 02/35636 | | | 5/2002 |

OTHER PUBLICATIONS

Nomoto et al., "Photocurrent generation system incorporated with antenna function," Chemistry Communication 2002, 1104-1105.
Ogawa et al., "Formation of Giant Supramolecular Porphyrin Array by Self-Coordination," Angew. Chem. Int. Ed. 2000,39 4070-4073.
Salama et al., "Remarkable oxygen promotion of the selective reduction of nitric oxide by hydrogen over Au/NaY and Au/ZSM-5 zeolite catalysts," Chem. Commun. 1997, 105-106.
Takahashi et al., "Hexameric Macroring of Gable-Porphyrins as a Light-Harvesting Antenna Mimic," J. Am. Chem. Soc. 2003, 125, 2372-2373.
Tang, C.W., "Two-layer organic photovoltaic cell," Applied Physics Letters, 1986, 48, pp. 183-185.
Yu et al., "Polymer Photovoltaic Cells: Enhanced Efficiencies via a Network of Internal Donor-Acceptor Heterojunctions," Science 1995, 1789-1791.
English abstract for JP 2001-253883, Sep. 2001.
English abstract for JP 2002-335004, Nov. 2002.
Japanese Office Action issued Aug. 25, 2009, for corresponding Japanese Patent Application JP 2004-010068.

* cited by examiner

R = alkyl, aryl., (CH$_2$)$_2$CO$_2$CH$_2$CH=CH$_2$

PHOTOELECTRIC TRANSFER MATERIAL, MANUFACTURING METHOD THEREOF, PHOTOELECTRIC TRANSFER ELEMENT AND MANUFACTURING METHOD THEREOF

CROSS REFERENCE TO RELATED APPLICATION

This application claims priority to Japanese Patent Document No. 2004-010068, filed on Jan. 19, 2004 with the Japanese Patent Office, which disclosure in its entirety is hereby incorporated by reference.

BACKGROUND OF THE INVENTION

The present invention relates to a photoelectric transfer material, its manufacturing method, photoelectric transfer element and its manufacturing method, especially suitable for application to organic solar cells, for example.

Existing solar cells using organic dyes are roughly classified by two types. Those of one type are dye-sensitized solar cells having a structure in which a dye is made to adhere on an oxide semiconductor on an electrode and an electrolyte is injected between the electrode and a counter electrode. Those of the other type are organic solar cells having a structure in which electron-acceptable compound of an organic dye such as phthalocyanine and pellerine or the like is deposited in form of a film on a light permeable electrode by vapor deposition or spin coating (Appl. Phys. Lett. 1986, 48, 183).

The former-type dye-sensitized solar cells have been subjected to vigorous studies by Gratzel et al. and have attained the efficiency around 10% (AM 1.5) (Chem. Commun. 1997, 105). However, because of the difficulty in sealing the electrolytic solution, it is difficult to employ this cell structure to flexible solar cells using a plastic substrate. Therefore, researches move forward to solidify electrolytes.

The latter-type organic solar cells could not exceed 1% in efficiency for a long time because of high internal resistance inherent to organic compounds and small thickness of the layer contributing to separation of electric charge. In 1995, however, Heeger et al. reported an organic cell made of a conductive polymer and a fullerene derivative. After the organic cell was proved to achieve much higher performance than conventional organic solar cells, researches of this line have become active. In conventional organic solar cells, cells were formed by depositing electron acceptors and dye molecules in form of layers. However, since separation of electrons occurs at the interface of these layers as explained above, only some of photons captured near the interface could be effective for separation of electrons. Moreover, since the charge generated thereby had to move in the high-resistance organic substance to respective electrodes, internal resistance of the cell increased and made it difficult to extract a large current. In the above-introduced organic solar cell composed of the conductive polymer and the fullerene derivative, the polymer and the fullerene derivative merge in the molecular level, and result in successfully forming a very large interface. With organic solar cells of this type, efficiency around 2.5% (AM 1.5) has been reported heretofore in the system of MDMO-PPV:PDBM (Appl. Phys. Lett. 78(6), 841-843; U.S. Pat. No. 5,331,183; and Science, 1995, 1789).

All of solar cells of this type are composed of flexible organic compounds and have various advantages, namely, excellent flexibility, no requirement of annealing process such as calcination, readiness for being made by coating process such as spin coat method except the back electrode (such aluminum), dependency of the potential simply upon the potential difference between the conductive polymer as the electron donor and the electron acceptor, possibility of making a large interface because of the bulk heterojunction.

Japanese Patent Laid-open Publication No. JP2002-335004A describes introducing a kind of porphyrin as a photosensitizer into a photoelectric transfer material containing a conductive polymer as the electron donor, spherical shell-shaped carbon as the electron acceptor, linear or tubular carbon as the electron transporter. This publication, however, does not describe introduction of antenna porphyrin aggregates as a kind of porphyrin.

A method of forming annular associated porphyrin is disclosed in J. Am. Chem. Soc. 2003, 125(9), 2372-2373. Methods of cross-linking porphyrin units are disclosed in Japanese Patent Laid-open Publications No. JP2002-281616A and No. 2003-54719A. Characteristics of porphyrin aggregates are described in Angew. Che. Int. Ed. 2000, 39(22), 4070-4073 and Chem. Commun. 2002, 1104-1105.

However, the above-mentioned systems have disadvantages such as still large electric resistance of films (trade-off of thickness of films and light absorbability), inefficient use of sunlight because of mismatch of absorption spectrum of MDMO-PPV with sunlight spectrum, instability in air because of liableness to oxidation of MDMO-PPV and their still high costs.

SUMMARY OF THE INVENTION

The present invention relates to a photoelectric transfer material, its manufacturing method, photoelectric transfer element and its manufacturing method, especially suitable for application to organic solar cells, for example.

The invention in an embodiment provides a photoelectric transfer material having low electric resistance, high photoelectric transfer efficiency by efficient use of sunlight and stability, and to provide its manufacturing method, photoelectric transfer element using the photoelectric transfer material and manufacturing method of the photoelectric transfer element.

According to an embodiment of the invention, there is provided a photoelectric transfer material including:

an electrically conductive polymer;

an electron acceptor; and an antenna porphyrin aggregate.

According to another embodiment of the invention, there is provided a method of manufacturing a photoelectric transfer material characterized in forming the photoelectric transfer material by using an electrically conductive polymer, an electron acceptor and an antenna porphyrin aggregate.

According to yet another embodiment of the invention, there is provided a photoelectric transfer element including:

a photoelectric transfer material including an electrically conductive polymer, an electronic acceptor and an antenna porphyrin aggregate.

According to still yet another embodiment of the invention, there is provided method of manufacturing a photoelectric transfer element characterized in forming a photoelectric transfer element by using an electrically conductive polymer, an electron acceptor and an antenna porphyrin aggregate.

In an embodiment, the photoelectric transfer material is composed of a conductive polymer, electron acceptor, and antenna porphyrin aggregate. If necessary, it may include one or more other kinds of compounds or the like.

Any suitable conductive polymer can be utilized, examples of which are shown below.

(1) poly(2-methoxy-5-2'-ethyl)-hexyloxy-p-phenylenevinylene (MEH-PPV)

[Formula 1]

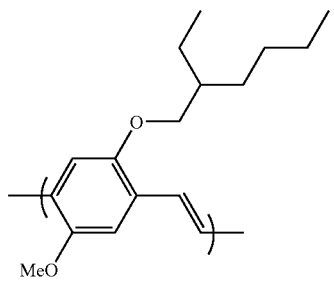

(2) poly(2-methyloxy,5-(3,7-dimethyloctyloxy))-p-phenylenevinylene (MDMO-PPV)

[Formula 2]

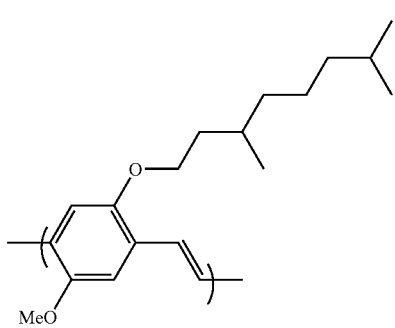

(3) poly(3-octylthiopene) (P3OT)

[Formula 3]

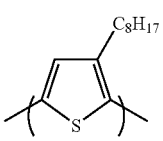

(4) poly(3-hexylthiopene) (P3HT)

[Formula 4]

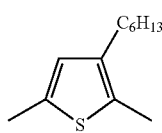

(5) poly(2,7-(9-(2'-ethylhexyl)-9-hexyl-fluorene)-alt-5,5-(4',7'-di-2-thienyl-2',1',3'-benzothiadiazole) (PFDTBT)

[Formula 5]

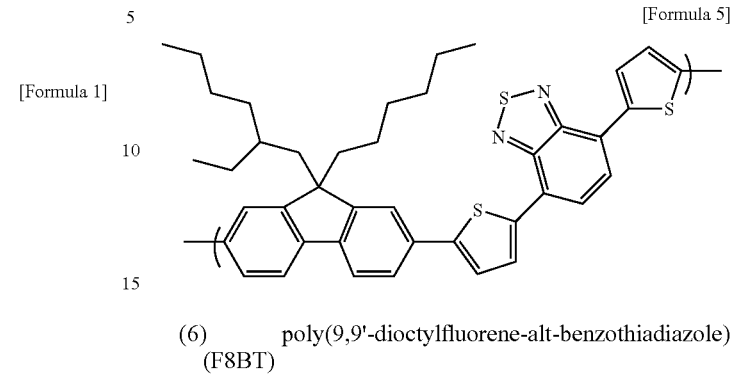

(6) poly(9,9'-dioctylfluorene-alt-benzothiadiazole) (F8BT)

[Formula 6]

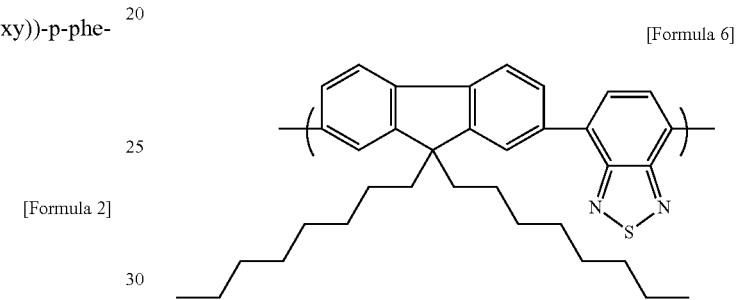

Any suitable material can be utilized for the electron acceptor. Examples include low molecular-weight electron acceptors such as fullerene derivatives like $C_{60}$, $C_{70}$, $C_{74}$, $C_{76}$, $C_{82}$, $C_{84}$, and the like.

The antenna porphyrin aggregate in an embodiment includes as its unit a dimer structure having two porphyrin rings combined in a meso position and imidazole radicals having coordinate nitrogen atoms in meso positions at opposite position from the porphyrin-to-porphyrin bond as shown in FIG. 1A. A metal ion (M) at the center of one dimer porphyrin ring and one of imidazole rings of another dimer are in complementary coordination bond. As a result of the complementary coordinate bond, association constant of the antenna porphyrin aggregate is very large and provides a linear association as shown in FIG. 1B. The antenna porphyrin aggregate can be formed in other than the linear structure by slightly modifying the above structure. For example, as shown in FIG. 2A, a dimer of porphyrin rings bonded at 120 degrees by introducing an m-phenylene radical therebetween instead of directly bonding two porphyrin rings. This structure forms annular associated porphyrin by complementary coordinate bonding as shown in FIG. 2B (Japanese Patent Laid-open Publication No. JP2001-21388A). These associates are known to be very stable in a nonpolar solvent containing no coordinate substance. Also known is the method of cross-linking porphyrin units as shown in FIG. 3 to stabilize the structure even more (Japanese Patent Laid-open Publications No. JP2002-281616 and No. JP2003-54719). Antenna porphyrin aggregates exhibit noticeable shifting of long wavelengths in the absorption band called Q band up to aggregates of approximately eight unit molecules, but aggregates of more unit molecules exhibit almost no changes in absorption band.

These antenna porphyrin aggregates are known having the following features (Angew. Che. Int. Ed. 2000, 39(22), 4070-

4073; and Japanese Patent Laid-open Publications No. JP2001-21388 and No. JP2001-253883).

They form associates in nonpolar solvents already under concentration equal to or lower than $5.5 \times 10^{-9}$M.

They form associates of 400 or more unit molecules in maximum in chloroform not containing alcohol.

The larger the associate, the absorption peak of the long wavelength side of division of the Soret band caused by interaction of exciters shifts to longer wavelengths. This makes it possible to use light of wider wavelengths.

Antenna porphyrin aggregate shown in FIG. 1B or 2B may be used directly, or may be reduced to a lower molecular form. Thereby, light absorption spectrum can be adjusted. For this purpose, the antenna porphyrin aggregate may be modified with a base. More specifically, as shown in FIG. 4, antenna porphyrin aggregate having a linear chain structure shown in FIG. 1B may be introduced into 3 weight % pyridine solution at room temperature to bring about reaction as shown in FIG. 4. Thereby, antenna porphyrin aggregate can be cut to a lower molecular structure under the action of pyridine.

The photoelectric transfer element can be made in various forms for respective purposes, and it is not limited to a specific form.

In an embodiment, the photoelectric transfer element is a solar cell. However, various kinds of optical sensors are other examples of applications for the photoelectric transfer element.

The above-explained technique for making the photoelectric transfer material composed of conductive polymer, electron acceptors and antenna porphyrin aggregate is applicable not only to photoelectric transfer elements but also to all electronic devices using photoelectric transfer materials, such as electronic circuit having photoelectric transfer portions.

According to another embodiment of the invention, there is provided an electronic device that includes using a photoelectric transfer material including an electrically conductive polymer, an electron acceptor and an antenna porphyrin aggregate.

According to another embodiment of the invention, there is provided a method of manufacturing an electronic device using a photoelectric transfer material, that includes forming the photoelectric transfer material by using an electrically conductive polymer, an electron acceptor and an antenna porphyrin aggregate.

The electronic device and method of manufacturing same can be utilized according to various embodiments as discussed above and further described in detail below.

In the present invention having the above-summarized configuration, the antenna porphyrin aggregate contained in the photoelectric transfer material is made by coordinate bonding of porphyrin. The coordinate bonding brings about intensive interaction between transition dipole moments of porphyrin. Here is realized division of the absorption wavelength to a longer wavelength, quick shift of light energy (shift of excited energy) and excellent photoelectric transferability inside the porphyrin aggregate. Additionally, relatively wide absorption band of the antenna porphyrin aggregate enables efficient collection of light. In addition, photo-excited antenna porphyrin aggregate has a potential sufficient for deoxidizing electron acceptors such as fullerene derivatives, for example, and holed produced have a potential sufficient for oxidizing the conductive polymer.

Furthermore, since antenna porphyrin aggregate has a longer wavelength absorption band than normal conductive polymers, it can absorb lower-energy photons. Therefore, antenna porphyrin aggregate is not only elongated in lifetime by nonlocalization of the resulting excited state, but also enhanced in electron transfer efficiency by transfer of exciters to optimum positions for electron transfer to electron acceptors. The holes produced (porphyrin cation radicals) are stabilized by face-to-face close-bonded porphyrin molecules, and stable charge-separated state is realized by movement in antenna porphyrin aggregate.

Since antenna porphyrin aggregate has a large absorbency, the photoelectric transfer material can be thinned more. This makes it possible to reduce the electric resistance of the photoelectric transfer material and to take out electric charges more effectively.

Furthermore, since antenna porphyrin exhibits good compatibility with conductive polymer and electron acceptors, it is possible to obtain photoelectric transfer material having a small, uniform domain structure, and it contributes to increasing the area of the interface between the conductive polymer and the electron acceptor.

Moreover, since the conductive polymer contributes to stabilization of antenna porphyrin aggregate, stability of the photoelectric transfer material is enhanced.

According to the present invention in an embodiment, it is possible to obtain a photoelectric transfer material low in electric resistance, high in photoelectric transfer efficiency because of high sunlight usage efficiency, and stable, and hence possible to realize a photoelectric transfer element or electron device exhibiting high photoelectric transfer efficiency by using the excellent photoelectric transfer material.

Additional features and advantages of the present invention are described in, and will be apparent from, the following Detailed Description of the Invention and the figures.

DETAILED DESCRIPTION OF THE INVENTION

Figures 1A, 1B:
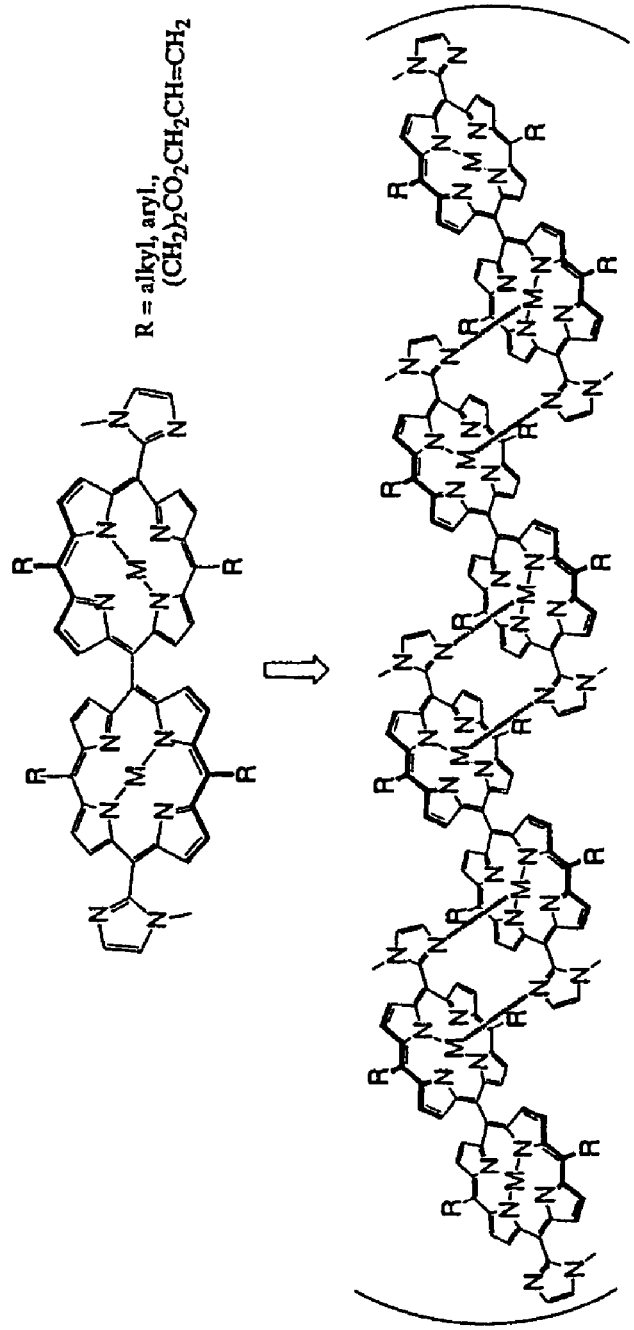
FIGS. 1A and 1B are a schematic diagram showing a structure of antenna porphyrin aggregates.
Figure 2A:
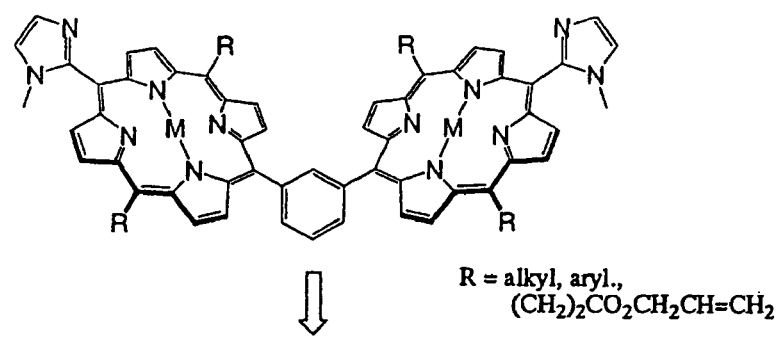
FIGS. 2A and 2B are a schematic diagram showing a structure of antenna porphyrin aggregates.
Figure 2B:
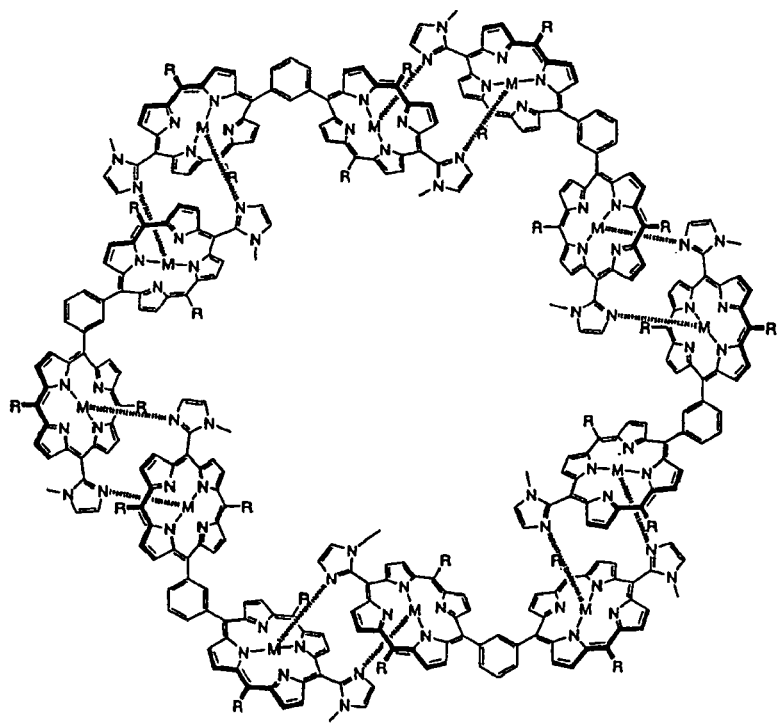
Figure 3:
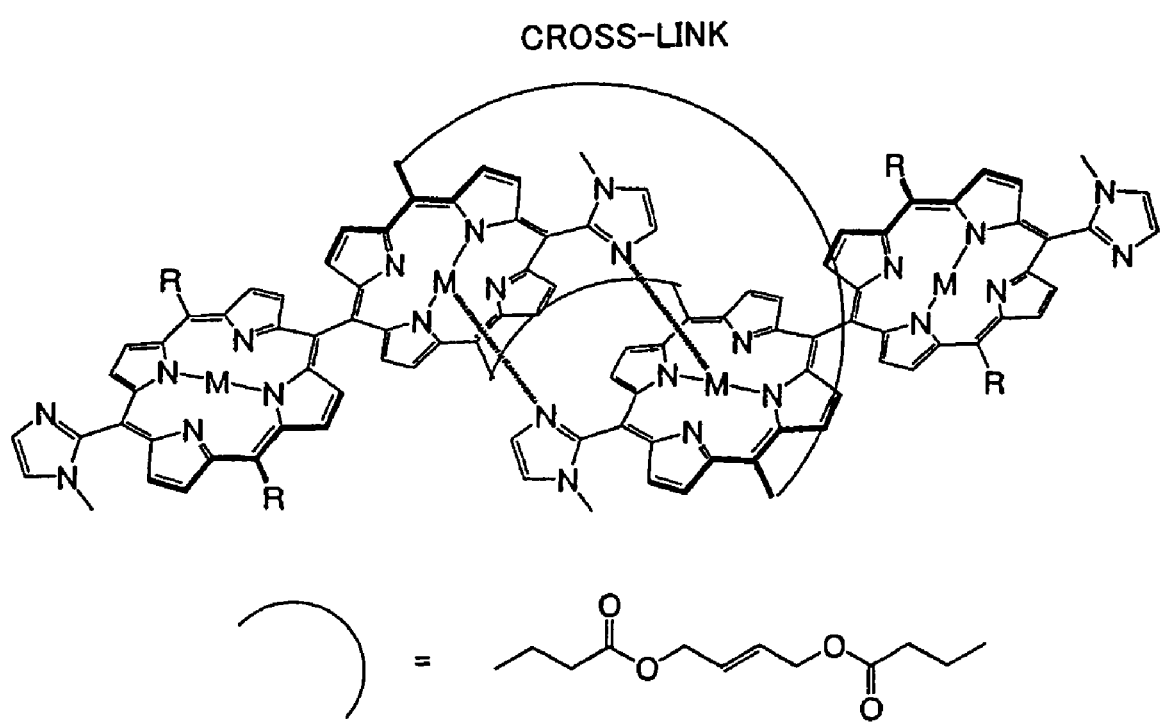
FIG. 3 is a schematic diagram showing a cross link of porphyrin units in antenna porphyrin aggregate.
Figure 4:
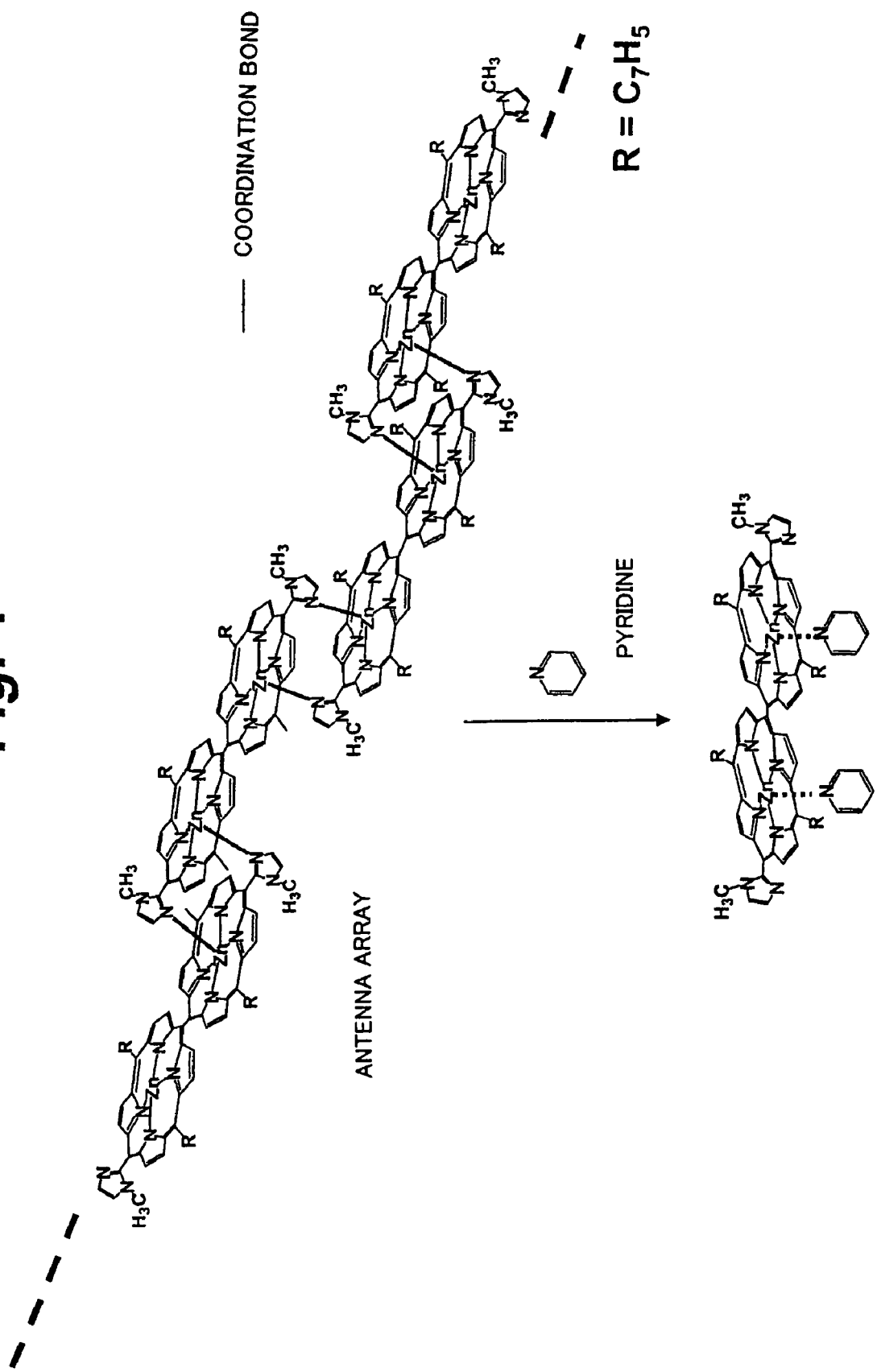
FIG. 4 is a schematic diagram used to explain cutting of antenna porphyrin aggregate by a base.

The present invention relates to a photoelectric transfer material, its manufacturing method, photoelectric transfer element and its manufacturing method, especially suitable for application to organic solar cells, for example.

Embodiments of the present invention will now be explained below with reference to the drawings. In all figures showing embodiments of the invention, identical or equivalent portions are labeled with common reference numerals.

Figure 5:
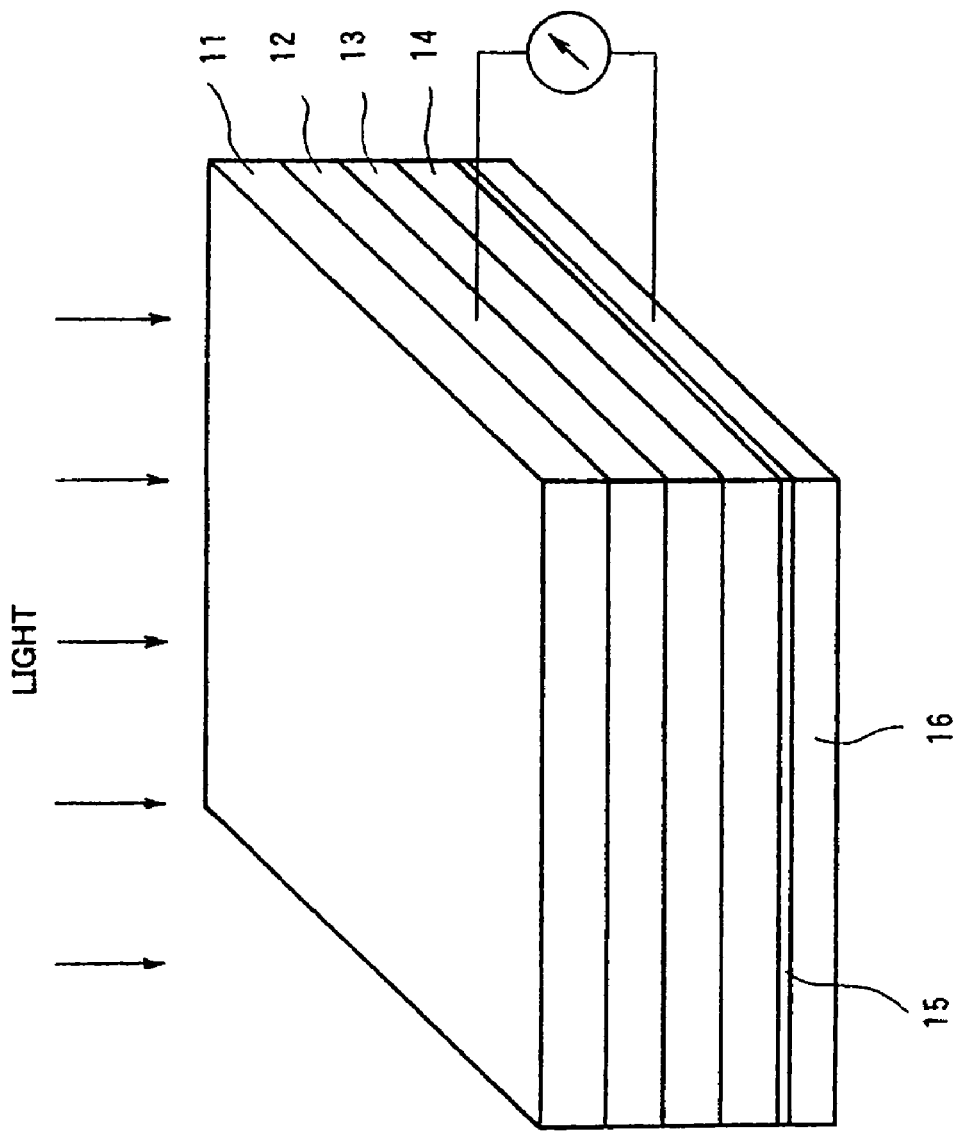
FIG. 5 is a perspective view of an organic photoelectric transfer element according to an embodiment of the invention.

FIG. 5 shows an organic photoelectric transfer element according to an embodiment of the invention.

As shown in FIG. 5, the organic photoelectric transfer element has a structure sequentially stacking on a transparent substrate 11 a transparent electrode 12, transparent conductive film 13, photoelectric transfer layer 14, intermediate layer 15 and electrode 16.

Material of the transparent substrate 11 may be chosen from various transparent base materials, preferably excellent in blockability against moisture and gas outside the organic photoelectric transfer element, resistance to solvent, anti-weatherability, and so on. Non-limitative examples of the transparent support substrate are transparent organic substrates of quartz, glass, or the like, as well as transparent plastic substrates of polyethylene terephthalate, polyethylene naphthalate, polycarbonate, polystyrene, polyethylene, polypropylene, polyphenylene sulfide, polyvinylidene fluoride, tetra acetyl cellulose, phenoxy bromide, various kinds of aramide, kinds of polyimide, kinds of polystyrene, kinds of polyalylate, kinds of polysulfon, kinds of polyolefin, and the like. Taking the workability, lightness in weight and flexibility into consideration, transparent plastic substrate represented by polyethylene terephthalate, for example, are especially desirable for use as the transparent substrate 11. Thickness of the transparent substrate 11 may be determined freely depending on light permeability and blockability between inside and outside of the organic transparent transfer element.

Known and suitable materials can be utilized as the material of the transparent electrode 12. More specifically, Indium-tin complex oxide (ITO), fluorine-doped $SnO_2$(FTO) and $SnO_2$ are usable materials although not limitative, and combinations of two or more kinds of those materials are usable as well.

An example of the material of the transparent conductive layer 13 is a transparent conductive polymer. The transparent conductive layer 13 may be 80 to 100 thick approximately.

Figure 6:
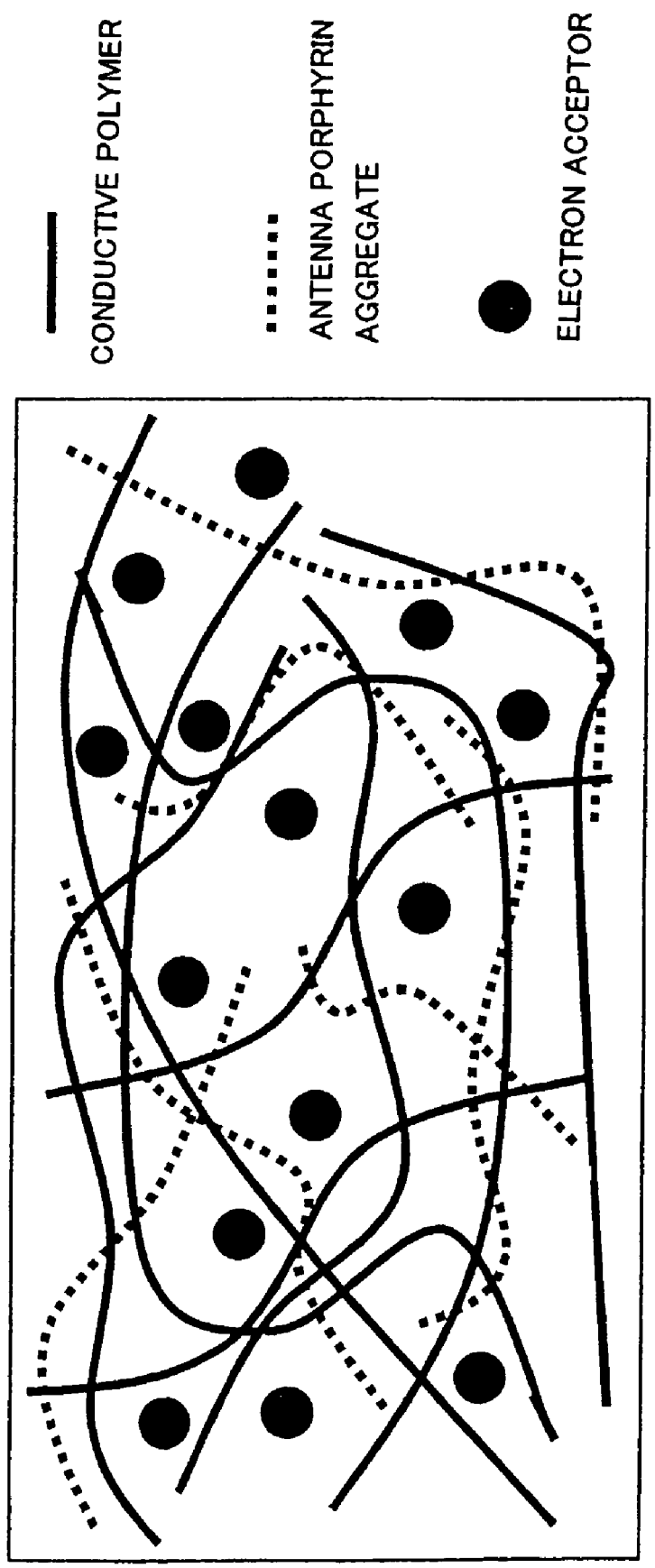
FIG. 6 is a schematic diagram showing a structure of photoelectric transfer layer in the organic photoelectric transfer element according to an embodiment of the invention.

As the material of the photoelectric transfer layer 14, here is used a combination of a conductive polymer, low molecular-weight electron acceptor and antenna porphyrin aggregate. As the conductive polymer, low molecular-weight electron acceptor and antenna porphyrin aggregate, the above-introduced materials are usable. The photoelectric transfer layer 14 may be 100 nm thick approximately. FIG. 6 schematically shows detailed structure of the photoelectric transfer layer 14. In FIG. 6, the conductive polymer is shown by the solid line, the low molecular-weight electron acceptor by black dots, and antenna porphyrin aggregate by the broken line.

The intermediate layer 15 is used for stabilization of the photoelectric transfer layer 14 and electric conduction between the photoelectric transfer layer 14 and the electrode 16. The intermediate layer 15 may be made of lithium fluoride (LiF), for example, and may be 0.6 nm thick approximately.

Essentially, the electrode 16 may be made of any conductive material. An example, however, is a metal such as Al. The electrode 16 may be 80 nm thick approximately.

Next explained are operations of the organic photoelectric transfer element.

As shown in FIG. 5, when light enters into the photoelectric transfer layer 14 through the transparent substrate 11 and through the transparent electrode 12 and the transparent conductive layer 13, electron-hole pairs are generated, and as a result of their charge separation, an electromotive force is generated between the transparent electrode 12 and the electrode 16. In this manner, photoelectric transfer takes place.

Figure 7:
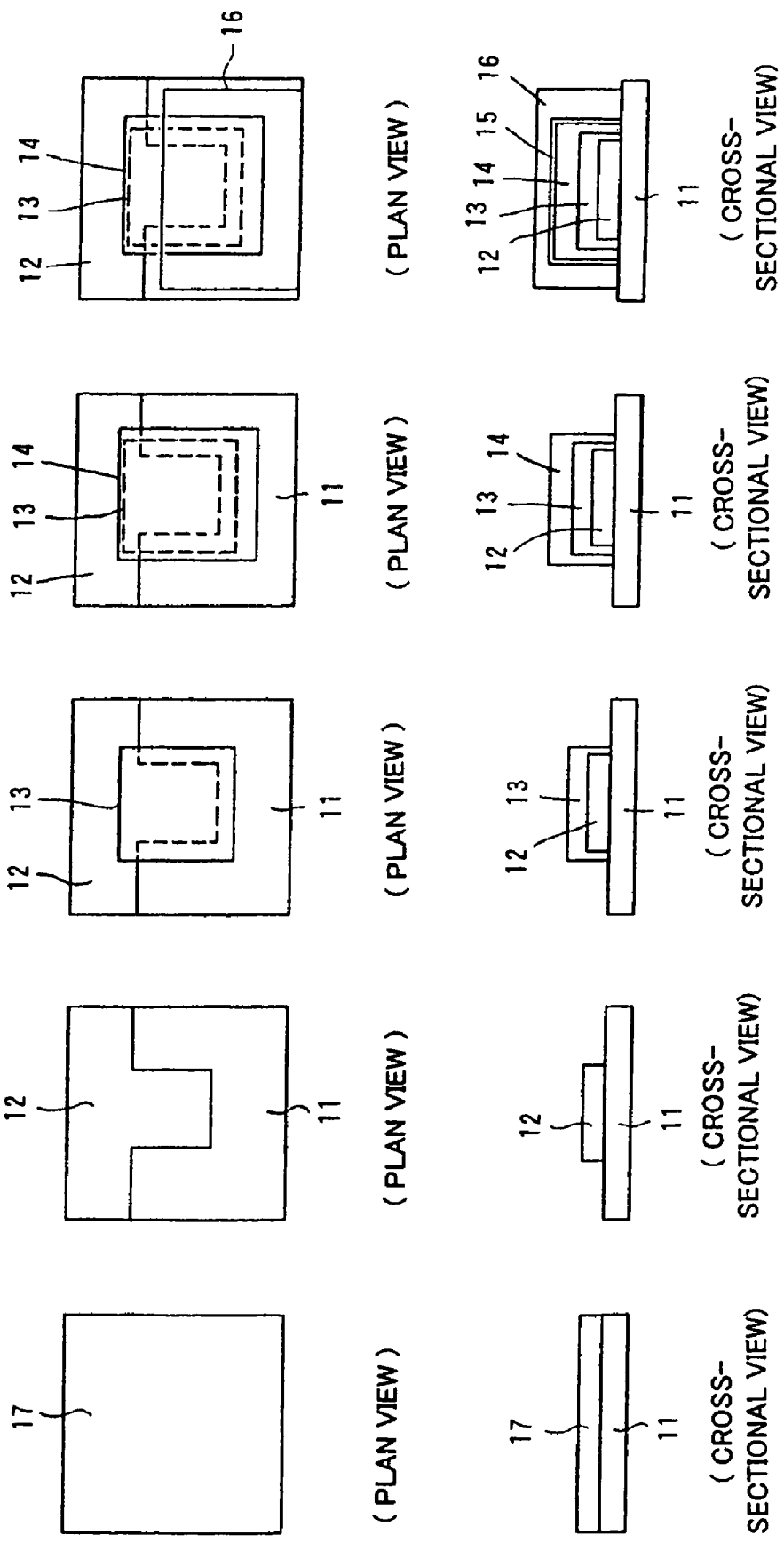
FIGS. 7A to 7E are cross-sectional views illustrating a manufacturing method of the organic photoelectric transfer element according to an embodiment of the invention.

Next explained is a manufacturing method of the organic photoelectric transfer element. FIGS. 7A through 7E show steps of the manufacturing method in order. After the transparent conductive film 17 is formed on the entire surface of the transparent substrate 11, it is patterned into a predetermined geometry. As shown in FIG. 7B, the transparent electrode 12 is formed.

In the next step shown in FIG. 7C, the transparent conductive film 13 is formed to partly overlap the transparent electrode 12.

In the next step shown in FIG. 7D, the photoelectric transfer layer 14 is formed to cover the transparent conductive film 13.

In the next step shown in FIG. 7E, the intermediate layer 15 and the electrode 16 are formed sequentially to cover the photoelectric transfer layer 14.

As a result, the organic photoelectric transfer element according to an embodiment is completed.

As explained above, according to an embodiment, the structure of the photoelectric transfer layer 14, composed of a conductive polymer, low molecular-weight electron acceptor and antenna porphyrin aggregate, provides the following advantages. Because of the absorption spectrum of the photoelectric transfer layer 14 matching the sunlight spectrum, the sunlight usage efficiency is enhanced. In addition, because of the large absorbance of the antenna porphyrin aggregate, the photoelectric transfer layer 14 can be decreased in thickness as compared to the thickness of the conventional photoelectric transfer layer that is composed of a conductive polymer and a low molecular-weight electron acceptor compound. For example, the photoelectric transfer layer can be decreased in thickness that is about one half the thickness of the conventional thickness according to an embodiment. This enables significant reduction of the electric resistance of the photoelectric transfer layer 14, and enhancement of the efficiency of electron transfer to the electron acceptor. As such, the organic photoelectric transfer element having a high sunlight usage efficiency, high photoelectric transfer efficiency and high performance can be provided.

EXAMPLES

A square polyethylene terephthalate (PET) film with an ITO film sized 25 mm long on each side and the sheet resistance of 10 ohms/square was used as the transparent electrode 11 and the transparent conductive film 17, respectively. A mask (not shown) of a predetermined geometry was formed on the ITO film. Thereafter, the work substrate was immersed in 1 N hydrochloric acid for one hour to pattern the ITO film to obtain the transparent electrode 12.

On the PET film having formed the transparent electrode 12 of ITO film, 1.3 weight % poly(styrenesulfonate)/poly(2, 3-dihydrothieno)[3,4-b]-1,4-dioxin) (hereafter called [PEDOT/PSS] was coated by spin coating, and it was dried at 120° C. for 30 minutes to obtain a PEDOT/PSS film having a thickness of 100 nm approximately and to use is as the transparent conductive film 13.

Further, a mixed solution of MEH-PPV, antenna porphyrin aggregate and PCBM (by the ratio of 1:1:4 in weight) (under chlorobenzene as the solvent) is spin-coated over an area slightly larger than the PEDOT/PSS film. Thereafter, the mixed solution was dried for one hour under a nitrogen gas flow, and additionally dried under reduced pressure ($<10^{-3}$ P) at the room temperature for three hours to obtain the photoelectric transfer layer 14. Synthesis of the antenna porphyrin aggregate was conducted according to the synthesis provided in Chem. Commun. 2002, 1104-1105. As the mixed solution of MEH-PPV, antenna porphyrin aggregate and PCBM, a material containing them by 12.5 mg, 12.5 mg and 50 mg, respectively, in 5.0 mL of chlorobenzene was used. The photoelectric transfer layer 14 thus obtained is called Sample A.

Furthermore, a 0.6 nm thick LiF film as the intermediate layer 15 and a 125 nm thick Al film as the electrode 16 were sequentially deposited by vapor deposition.

In this manner, an organic photoelectric transfer element was prepared.

As a comparative example, a photoelectric transfer layer made was prepared by coating a mixed solution of MEH-PPV and PCBM not containing porphyrin component by spin coating instead of the mixed solution of MEH-PPV, antenna porphyrin aggregate and PCBM. More specifically, a MEH-PPV/PCBM mixed solution containing MEH-PPV and PCBM by the ratio of 15 mg:60 mg in 5.0 mL of chlorobenzene. The photoelectric transfer layer thus made is called Sample B.

Sample A and Sample B were coated on glass plates (MATSUNAMI MICROSLIDE GLASS 29112) to measure ultraviolet visible absorption spectrums of their photoelectric layers.

Figure 8:
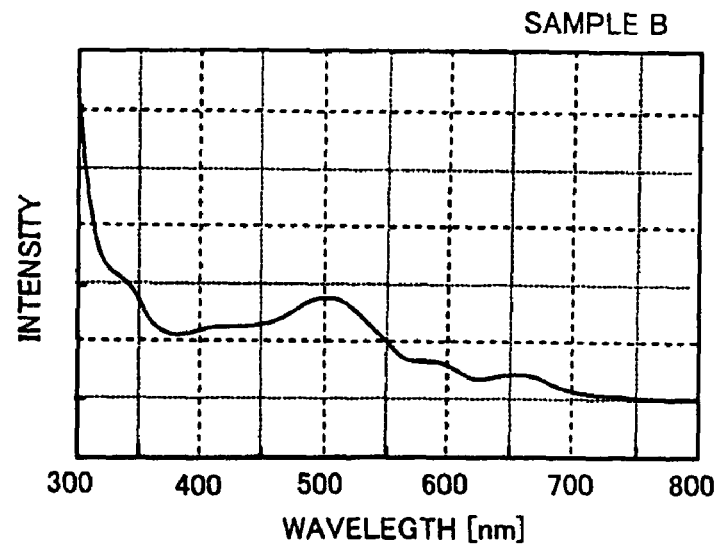
FIG. 8 is a schematic diagram showing a result of measurement of UV-vis spectrum of a photoelectric transfer layer composed of MEH-PPV, PCBM and antenna porphyrin aggregate.
Figure 9:
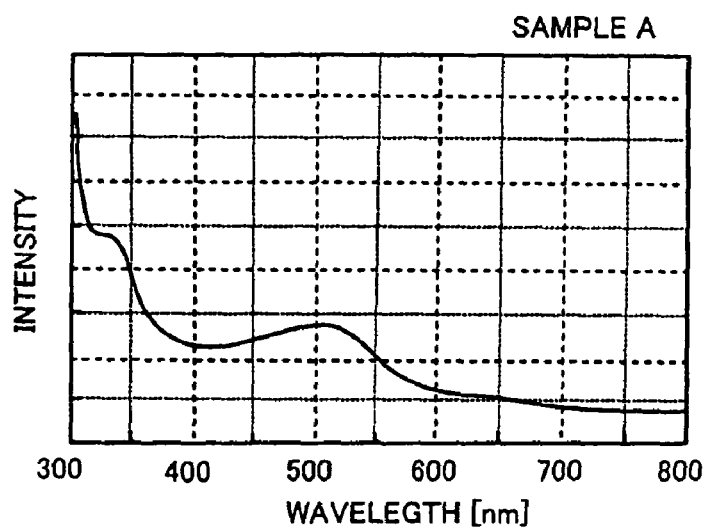
FIG. 9 is a schematic diagram showing a result of measurement of Uv-vis spectrum of a photoelectric transfer layer composed of MEH-PPV and PCB.
Figure 10:
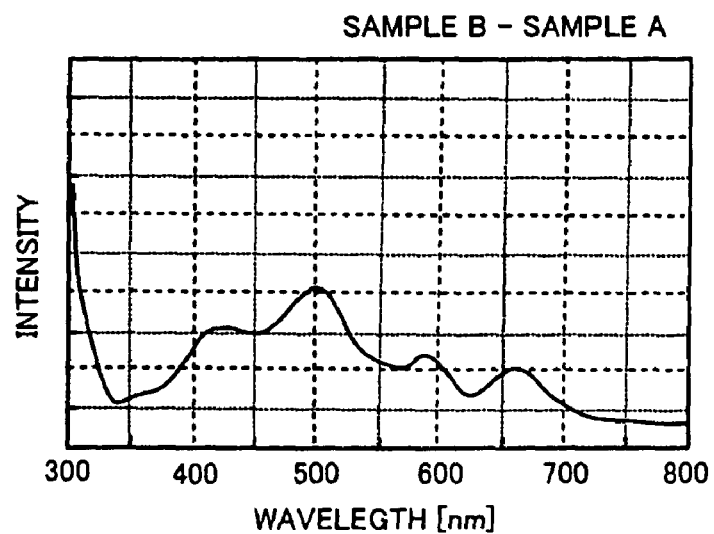
FIG. 10 is a schematic diagram showing a differential spectrum between the UV-vis spectrum of FIG. 8 and the UV-vis spectrum of FIG. 9.

FIGS. 8 and 9 show UV-vis spectrums of Sample A and Sample B, respectively. The UV-vis spectrum of Sample B (FIG. 8), not added with antenna porphyrin aggregate, exhibited a broad absorption spectrum having peaks at the wavelength of 505 nm derived from MEH-PPV. In contrast, in the UV-vis spectrum of Sample A (FIG. 9), added with antenna porphyrin aggregated, absorption peaks derived from the antenna porphyrin aggregate were observed in addition to the absorption peaks of the wavelength 503 nm derived from MEH-PPV. Thus, the absorption of the photoelectric transfer layer in Sample A was confirmed to shift to longer wavelengths significantly. FIG. 10 showing the differential spectrum (Sample B—Sample A) demonstrates that a spectrum coinciding with the absorption spectrum of the antenna porphyrin aggregate was obtained. This means that, in the ground state, strong interaction does not occur between the porphyrin and MEH-PPV or PCBM. Therefore, the photoelectric transfer layer is assumed to have a structure desirable for charge separation. Additionally, absorbance of the photoelectric transfer layer in Sample A became higher as much as approximately 10 times the absorbance of Sample B.

Having described specific preferred embodiments of the present invention with reference to the accompanying drawings, it is to be understood that the invention is not limited to those precise embodiments, and that various changes and modifications may be effected therein by one skilled in the art without departing from the scope or the spirit of the invention as defined in the appended claims.

For example, numerical values, structures, materials and processes proposed in conjunction with the present invention according to various embodiments discussed above are illustrative, and other numerical values, structures, materials and processes may be used, if necessary.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. An electronic device comprising:

a transparent substrate;

a transparent electrode formed directly on and contacting the transparent substrate to partially cover the transparent substrate;

a transparent conductive film formed directly on and contacting the transparent electrode and the transparent substrate to partially overlap the transparent electrode and partially cover the transparent substrate;

a photoelectric transfer layer formed directly on and contacting the transparent electrode, the transparent substrate and the transparent conductive film to cover the transparent conductive film and portions of the transparent electrode and the transparent substrate, and including a photoelectric transfer material, said photoelectric transfer material comprising an electrically conductive polymer, an electron acceptor and an antenna porphyrin aggregate, the antenna porphyrin aggregate comprising approximately 8 or fewer unit molecules, wherein the electrically conductive polymer is poly(2-methoxy-5-2'-ethyl)-hexyloxy-p-phenylenevinylene

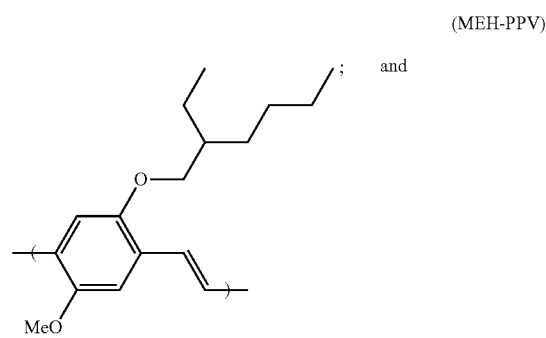

(MEH-PPV)

; and an intermediate layer and a second electrode formed sequentially to partially cover the photoelectric transfer layer and the transparent substrate, such that the intermediate layer directly contacts the photoelectric transfer layer, wherein the electrically conductive polymer, the antenna porphyrin aggregate, and the electron acceptor are combined in a ratio of about 1:1:4 by weight.

2. The electronic device according to claim 1, wherein the photoelectric transfer material is formed into a layer with a thickness of about 100 nm.

3. The electronic device according to claim 1, wherein the photoelectric transfer layer exhibits a shifting to longer wavelengths in an absorption band called Q band relative to a photoelectric transfer layer not including antenna porphyrin aggregates.

4. The electronic device according to claim 1, wherein the photoelectric transfer layer has an absorption spectrum that substantially matches a sunlight spectrum.

5. The electronic device according to claim 1, wherein in a UV-visible spectrum of the photoelectric transfer layer, there exist a plurality of absorption peaks in addition to an absorption peak derived from the (MEH-PPV).

6. A method of manufacturing an electronic device comprising:

providing a transparent substrate;

forming a transparent electrode directly on and contacting the transparent substrate to partially cover the transparent substrate;

forming a transparent conductive film directly on and contacting the transparent electrode and the transparent substrate so as to partially overlap the transparent electrode and partially cover the transparent substrate;

forming a photoelectric transfer layer directly on and contacting the transparent electrode the transparent substrate and the transparent conductive film so as to cover the transparent conductive film and portions of the transparent electrode and the transparent substrate, and including a photoelectric transfer material, said photoelectric transfer material including an electrically conductive polymer, an electron acceptor and an antenna porphyrin aggregate, the antenna porphyrin aggregate comprising approximately 8 or fewer unit molecules, wherein the electrically conductive polymer is poly(2-methoxy-5-2'-ethyl)-hexyloxy-p-phenylenevinylene

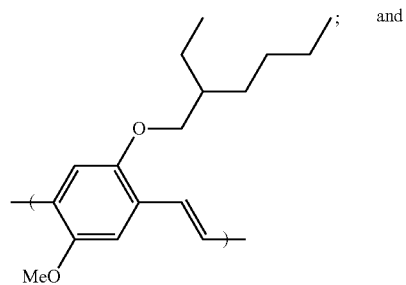

(MEH-PPV)

forming an intermediate layer and a second electrode sequentially to partially cover the photoelectric transfer layer and the transparent substrate, such that the intermediate layer directly contacts the photoelectric transfer layer, wherein the electrically conductive polymer, the antenna porphyrin aggregate, and the electron acceptor are combined in a ratio of about 1:1:4 by weight.

7. The method of manufacturing an electronic device according to claim 6, wherein the photoelectric transfer material is formed into a layer with a thickness of about 100 nm.

* * * * *